United States Patent
Ashby et al.

(10) Patent No.: US 8,617,170 B2
(45) Date of Patent: Dec. 31, 2013

(54) CUSTOMIZED PATIENT-SPECIFIC COMPUTER CONTROLLED CUTTING SYSTEM AND METHOD

(75) Inventors: Alan Ashby, York (GB); Said T. Gomaa, Fort Wayne, IN (US); Gordon Dodds, Feldkirchen (DE)

(73) Assignee: DePuy Synthes Products, LLC, Raynham, MA (US)

( * ) Notice: Subject to any disclaimer, the term of this patent is extended or adjusted under 35 U.S.C. 154(b) by 285 days.

(21) Appl. No.: 12/893,702

(22) Filed: Sep. 29, 2010

(65) Prior Publication Data

US 2012/0078254 A1   Mar. 29, 2012

(51) Int. Cl.
   A61F 5/00   (2006.01)

(52) U.S. Cl.
   USPC .............................. 606/88; 606/87

(58) Field of Classification Search
   USPC .................. 606/79–80, 86 R, 87–89, 96–98
   See application file for complete search history.

(56) References Cited

U.S. PATENT DOCUMENTS

| | | |
|---|---|---|
| 5,171,244 A | 12/1992 | Caspari et al. |
| 5,207,680 A | 5/1993 | Dietz et al. |
| 5,304,181 A | 4/1994 | Caspari et al. |
| 5,344,423 A | 9/1994 | Dietz et al. |
| 5,496,324 A | 3/1996 | Barnes |
| 5,601,563 A | 2/1997 | Burke et al. |
| 5,769,855 A | 6/1998 | Bertin et al. |
| 5,860,981 A | 1/1999 | Bertin et al. |
| 5,908,424 A | 6/1999 | Bertin et al. |
| 6,554,837 B1 * | 4/2003 | Hauri et al. ............... 606/87 |
| 7,608,079 B1 * | 10/2009 | Blackwell et al. ........... 606/87 |
| 7,695,477 B2 | 4/2010 | Creger et al. |
| 7,824,181 B2 | 11/2010 | Sers |
| 2003/0028196 A1 | 2/2003 | Bonutti |
| 2004/0243134 A1 | 12/2004 | Walker et al. |
| 2006/0200161 A1 | 9/2006 | Plaskos et al. |
| 2007/0270685 A1 | 11/2007 | Kang et al. |
| 2009/0228145 A1 | 9/2009 | Hodgson et al. |
| 2010/0087829 A1 | 4/2010 | Metzger et al. |

(Continued)

FOREIGN PATENT DOCUMENTS

WO   2004112620 A1   12/2004
WO   2009001083 A1   12/2008

OTHER PUBLICATIONS

European Search Report, European Patent Application No. 11175826.4-2310, Nov. 30, 2011, 6 pages.

(Continued)

Primary Examiner — Kevin T Truong
Assistant Examiner — Matthew Lawson
(74) Attorney, Agent, or Firm — Barnes & Thornburg LLP

(57) ABSTRACT

A customized patient-specific orthopaedic surgical system including a first surgical block, a second surgical block, and a computer-controlled milling machine. The first surgical block includes a first bone-facing surface having a first customized patient-specific negative contour to receive a first corresponding contour of a bone of a patient and a first mounting surface. The second surgical block includes a second bone-facing surface having a second customized patient-specific negative contour to receive a second corresponding contour of the bone of the patient and a second mounting surface to be separately mated with the first mounting surface. The computer-controlled milling machine includes a third mounting surface to be separately mated with the first mounting surface of the first surgical block.

11 Claims, 7 Drawing Sheets

(56) References Cited

U.S. PATENT DOCUMENTS

2010/0234850 A1    9/2010  Dees, Jr. et al.
2011/0257653 A1*  10/2011  Hughes et al. ............... 606/79
2012/0143198 A1*   6/2012  Boyer et al. ................. 606/87

OTHER PUBLICATIONS

Radermacher, German Version: Helmholtz Institute of Biomedical Technology, "Computer-Assisted Planning and Execution of Orthopedic Surgery Using Individual Surgical Templates", May 18, 1999.
Radermacher, English Translation: Helmholtz Institute of Biomedical Technology, "Computer-Assisted Planning and Execution of Orthopedic Surgery Using Individual Surgical Templates", May 18, 1999.
Radermacher et al., "Computer Assisted Orthopedic Surgery by Means of Individual Templates—Aspects and Analysis of Potential Applications—" Proceedings of the First International Symposium on Medical Robotics and Computer Assisted Surgery, vol. 1: Sessions I-III, MRCAS '94, Pittsburgh, PA, pp. 42-48 (Sep. 22-24, 1994).
Radermacher et al., "Computer-Integrated Orthopaedic Surgery: Connection of Planning and Execution in Surgical Intervention," Computer Integrated Surgery, 451-463, 1995.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher et al., "CT Image Based Planning and Execution of Interventions in Orthopedic Surgery Using Individual Templates—Experimental Results and a spects of Clinical Applications." In Nolte LP, Ganz, R. (eds). CAOS—Computer Assisted Orthopaedic Surgery. Bern, Hans Huber (in Press) 1998.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al., "Computer Assisted Matching of Planning and Execution in Orthopedic Surgery", IEEE, EMBS, San Diego, 1993, pp. 946-947.
Hafez et al., "Computer-assisted Total Kneed Arthroplasty Using Patient-specific Templating", Clin Orthopaedics and Related Research, 444, 184-192, 2006 (12 pages).
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Hazan, Eric J., M.D., "Computer-Assisted Orthopaedic Sugery, A New Paradigm," Techniques in Orthopaedics.RTM. vol. 18, No. 2, (2003) pp. 221-229.
Portheine, F., "CT-basierte Planung und DISOS-Schablonennavigation in der Kniegelenkendoprothetik," in Navigation und Robotic in der Gelenk—und Wirbelsaulenchirugie, Kapitel 32, Springer Verlag (2003) pp. 262-269.
Portheine, K., "Development of a clinical demonstrator for computer assisted orthopedic surgery with CT-image based individual ndividual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (Sep. 1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "Image Guided Orthopedic Surgery Using Individual Templates," Springer Berlin/Heidelberg, CVRMed-MRCAS'97, vol. 1205/1997 pp. 606-615).
Radermacher, Klaus, et al. "Computer Assisted Orthopaedic Individual Templates." Clinical Orthopaedics and Related Research. (Sep. 1998) No. 354; pp. 28-38.
Hafez et al., "Computer-Assisted Total Hip Arthroplasty: The Present and the Future", Future Rheumatol., vol. 1, pp. 121-131, 2006.
Portheine et al., In German: "Potentials of CT-based Planning and Template-based Procedure in Hip and Knee Surgery", Orth. Prac., vol. 36, pp. 786-791, 2000.
Birnbaum et al., "Computer-Assisted Orthopedic Surgery With Individual Templates and Comparison to Conventional Operation Method", Spine, vol. 26, No. 4, pp. 365-369, Feb. 2001.
Chelule et al., "Computer Aided Design of Personalized Jigs in Total Knee Replacement", $3^{rd}$ Annual Meeting of CAOS Int'l Proc., Spain, Jun. 18, 21, 2003, pp. 58-59.
Froemel et al., "Computer Assisted Template Based Navigation for Total Knee Replacement", Documents presented at CAOS on Jun. 17, 2001, 4 pages.
Hafez et al., "Computer Assisted Total Knee Replacement: Could a Two-Piece Custom Template Replace the Complex Conventional Instrumentations?", $4^{th}$ Annual Meeting of CAOS Int'l Proc., Chicago, Jun. 16-19, 2004, pp. 63-64.
Radermacher, "Computer Assisted Matching of Planning and Execution in Orthopedic Surgery", Slide Presentation, San Diego, Nov. 29, 1993, 22 pages.
Radermacher et al., "Computer Integrated Advanced Orthopedics (CIAO)", $2^{nd}$ European Conference on Eng. and Med., presented Apr. 26, 1993, 12 pages.
Radermacher, "Image Guided Orthopedic Surgery with Individual Templates", Helmhotz-Institute for Biomed. Eng., 2 pages, 1997.
Radermacher et al., In German: "Computer-assisted operative interventions in orthopedics—are there prospects for endoprosthetics as well?", Prac. Ortho., vol. 27, pp. 149-164, 1997.
Radermacher et al., English Translation with Certification: "Computer-assisted operative interventions in orthopedics—are there prospects for endoprosthetics as well?", Prac. Ortho., vol. 27, pp. 1-17, 1997.
Radermacher et al., "Computer Based Decision Support for the Planning of Contact Faces for Manual Registration with Individual Templates", Helmholtz-Institute for Biomed. Eng., 7 pages, 1997-98.
Radermacher, In German: "Computer-Based Decision Support in the Selection and Evaluation of Contact Surfaces for Manual Referencing", Lecture presented at Helmholtz Meeting '98 and OSS '98, 7 pages.
Radermacher, English Translation with Certification: "Computer-Based Decision Support in the Selection and Evaluation of Contact Surfaces for Manual Referencing", Lecture presented at Helmholtz Meeting '98 and OSS '98, 8 pages.
Radermacher et al., In German: "Computer-Assisted Planning and Operation in Orthopedics", Orth. Prac. $36^{th}$ year, pp. 731-737, Dec. 2000.
Radermacher et al., English Translation with Certification: "Computer-Assisted Planning and Operation in Orthopedics", Orth. Prac. $36^{th}$ year, pp. 731-737, Dec. 2000.
Staudte et al., English Translation with Certification: "Computer-Assisted Operation Planning and Technique in Orthopedics", North Rhine-Westphalia Acad. For Sciences, Lecture N.444, ISSN 0944-8799, 2000, 34 pages.

* cited by examiner

CUSTOMIZED PATIENT-SPECIFIC COMPUTER CONTROLLED CUTTING SYSTEM AND METHOD

CROSS-REFERENCE TO RELATED APPLICATIONS

Cross-reference is made to PCT International Application No. PCT/US2008/078143, which was filed on Sep. 29, 2008 and the entirety of which is incorporated herein by references.

TECHNICAL FIELD

The present disclosure relates generally to customized patient-specific orthopedic surgical systems, and, more specifically, to a customized patient-specific orthopedic surgical system for resecting a patient's bone and method of fabricating and using the same.

BACKGROUND

Joint arthroplasty is a well-known surgical procedure by which a diseased and/or damaged natural joint is replaced by a prosthetic joint. A typical knee prosthesis includes a tibial tray, a femoral component, a polymer insert or bearing positioned between the tibial tray and the femoral component, and, in some cases, a polymer patella button. To facilitate the replacement of the natural joint with the knee prosthesis, orthopedic surgeons use a variety of orthopedic surgical instruments such as, for example, cutting blocks, drill guides, milling guides, and other surgical instruments. Typically, the orthopedic surgical instruments are generic with respect to the patient such that the same orthopedic surgical instrument may be used on a number of different patients during similar orthopedic surgical procedures.

SUMMARY

According to one aspect of the disclosure, a customized patient-specific orthopedic surgical system is disclosed. The customized patient-specific orthopedic surgical system includes a first surgical block, a second surgical block configured to be coupled to the first surgical block, and a computer-controlled milling machine configured to be coupled to the first surgical block. The first surgical block includes a first bone-facing surface having a first customized patient-specific negative contour to receive a first corresponding contour of an anterior side of a bone of a patient and a first mounting surface. The second surgical block includes a second bone-facing surface having a second customized patient-specific negative contour to receive a second corresponding contour of a first end of the bone of the patient and a second mounting surface configured to be separately mated with the first mounting surface of the first surgical block. The computer-controlled milling machine includes a base having a third mounting surface configured to be separately mated with the first mounting surface of the first surgical block. In some embodiments, the first surgical block may further have a corresponding pair of mounting pin holes defined therein that extend from the first bone-facing surface to an outer surface of the first surgical block. The outer surface may be positioned opposite the first bone-facing surface.

In some embodiments, the first mounting surface may include a first locking structure, and the second mounting surface may include a second locking structure configured to couple with the first locking structure to secure the first surgical block to the second surgical block. Additionally, in some embodiments, the first locking structure may include a pair of mounting pins extending upwardly from the first mounting surface, and the second locking structure may include a pair of passageways defined in the second mounting surface that are sized and positioned to receive the pair of mounting pins. In some embodiments, the third mounting surface may include a second pair of passageways defined therein sized and positioned to receive the pair of mounting pins. In some embodiments, each mounting pin may be an externally threaded rod sized to receive a corresponding internally threaded nut.

In some embodiments, the orthopedic surgical system may further include an electronic controller electrically coupled to the computer-controlled milling machine. The electronic controller may include a processor and a memory device electrically coupled to the processor. The memory device may have stored therein a plurality of instructions, that, when executed by the processor, cause the processor to operate the computer-controlled milling machine to resect the bone of the patient in accordance with a predefined surgical plan.

According to another aspect, a method of performing an orthopedic surgical procedure on a bone of a patient is disclosed. The method includes securing a customized patient-specific surgical block to the bone of the patient such that a first end of the bone of the patient is received in a first customized patient-specific negative contour defined in the customized patient-specific surgical block and a first side of the bone of the patient is received in a second customized patient-specific negative contour defined in the customized patient-specific surgical block. The method also includes removing a first piece, which includes the first customized patient-specific negative contour, from a second piece of the customized patient-specific surgical block such that the second piece remains secured to the bone of the patient. The method further includes securing a computer-controlled milling machine to the second piece of the customized patient-specific surgical block after the first piece is removed, and operating the computer-controlled milling machine to resect the bone of the patient in accordance with a predefined surgical plan.

In some embodiments, the method may include generating a plurality of instructions based on the predefined surgical plan, and operating the computer-controlled milling machine may include commanding a processor of the computer-controlled milling machine to execute the plurality of instructions to resect the bone of the patient. In some embodiments, the method may further include generating the plurality of instructions based upon one or more medical images illustrating the bone of the patient. Additionally, in some embodiments, the method may include creating the predefined surgical plan based upon one or more medical images illustrating the bone of the patient.

In some embodiments, securing the customized patient-specific surgical block to the bone of the patient may include positioning the customized patient-specific surgical block in contact with the bone of the patient and inserting a pair of mounting pins into a pair of mounting pin holes defined in the second piece of the customized patient-specific surgical block. In some embodiments, removing the first piece of the customized patient-specific surgical block from the second piece includes removing the first piece from the bone of the patient after the mounting pins are inserted into the pair of mounting pin holes.

Additionally, in some embodiments, positioning the customized patient-specific surgical block may include positioning the customized patient-specific surgical block in contact with a femur of the patient, and operating the computer-controlled milling machine may include operating the computer-controlled milling machine to resect a distal end of the femur of the patient. In some embodiments, positioning the customized patient-specific surgical block may include positioning the customized patient-specific surgical block in contact with a tibia of the patient, and operating the computer-controlled milling machine may include operating the computer-controlled milling machine to resect a proximal end of the tibia of the patient.

According to another aspect, the customized patient-specific orthopedic surgical system includes a customized patient-specific surgical block and a computer-controlled milling machine. The customized patient-specific surgical block includes a first piece and a second piece. The first piece includes a first bone-facing surface having a first customized patient-specific negative contour to receive a first corresponding contour of a bone of a patient and a first locking structure. The second piece includes a second bone-facing surface having a second customized patient-specific negative contour to receive a second corresponding contour of the bone of the patient and a second locking structure to be separately mated with the first locking structure to secure the first piece to the second piece. The computer-controlled milling machine includes a third locking structure to be separately mated with the first locking structure.

In some embodiments, the customized patient-specific surgical block may be a customized patient-specific femoral surgical block. Additionally, in some embodiments, the customized patient-specific surgical block may be a customized patient-specific tibial surgical block.

In some embodiments, the first piece of the customized patient-specific surgical block may further include a pair of mounting pin holes defined therein, and the pair of mounting pin holes may extend from the first bone-facing surface to an outer surface positioned opposite the first bone-facing surface. In some embodiments, the orthopedic surgical system may further include an electronic controller electrically coupled to the computer-controlled milling machine. The electronic controller may include a processor, and a memory device electrically coupled to the processor. The memory device may have stored therein a plurality of instructions that, when executed by the processor, cause the processor to operate the computer-controlled milling machine in accordance with a predefined surgical plan.

BRIEF DESCRIPTION OF THE DRAWINGS

The detailed description particularly refers to the following figures, in which.

DETAILED DESCRIPTION OF THE DRAWINGS

Figure 1:
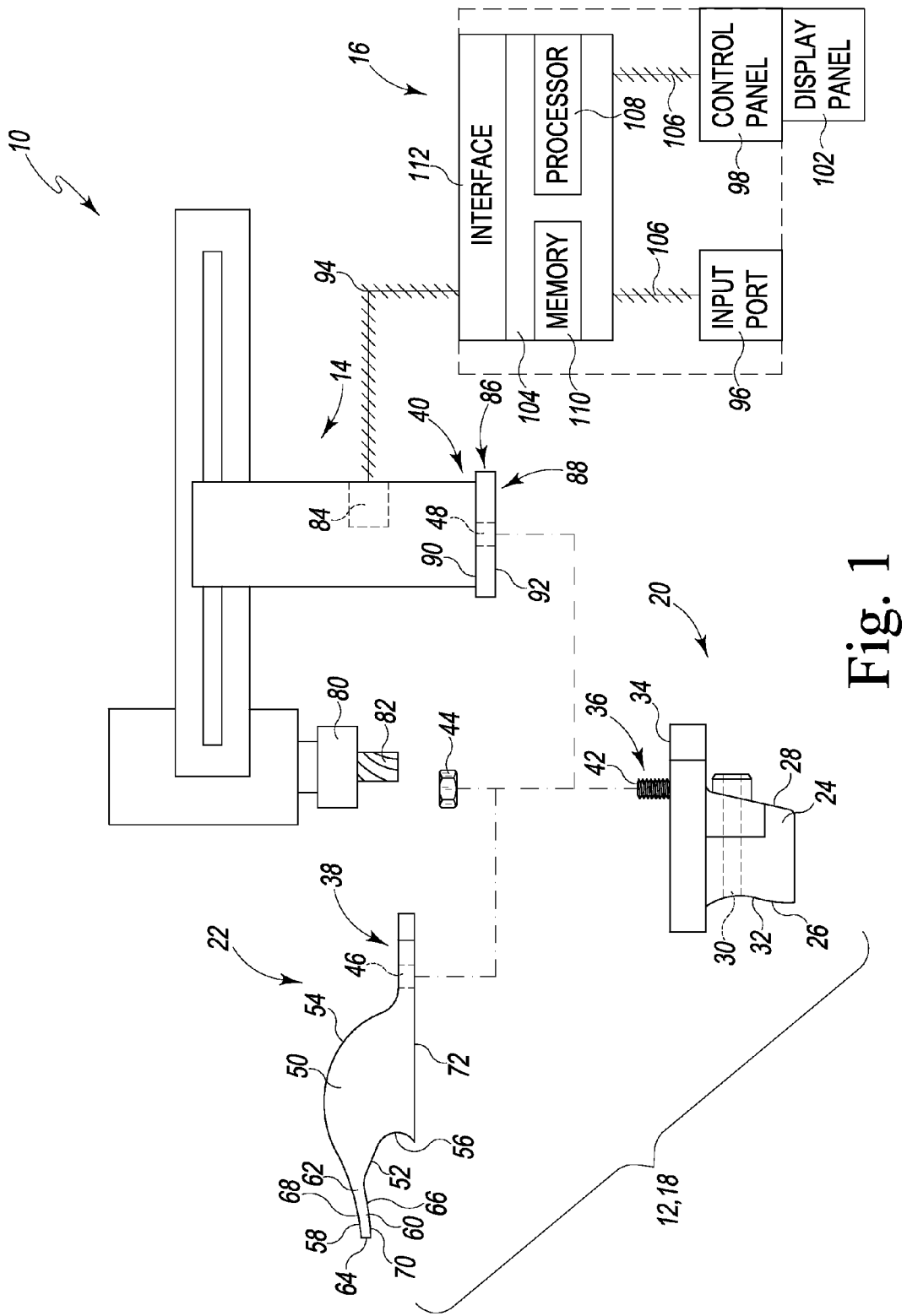
FIG. 1 is an exploded view of one embodiment of a customized patient-specific orthopedic surgical system showing a customized patient-specific surgical instrument and a computer-controlled milling machine.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a customized patient-specific orthopedic surgical system 10 is shown. The term "customized patient-specific orthopedic surgical system" as used herein refers to one or more customized patient-specific orthopedic surgical instruments for use by a surgeon in performing an orthopedic surgical procedure. What is meant herein by the term "customized patient-specific orthopedic surgical instrument" is a surgical tool for use by a surgeon in performing an orthopedic surgical procedure that is intended, and configured, for use on a particular patient. As such, it should be appreciated that a customized patient-specific orthopedic surgical instrument is distinct from standard, non-patient specific orthopedic surgical instruments that are intended for use on a variety of different patients. Additionally, it should be appreciated that a customized patient-specific orthopedic surgical instrument is distinct from orthopedic prostheses, whether patient-specific or generic, which are surgically implanted in the body of the patient. Rather, an orthopedic surgeon uses a customized patient-specific orthopedic surgical instrument to assist in the implantation of orthopedic prostheses.

In some embodiments, the customized patient-specific orthopedic surgical system may include a number of customized patient-specific orthopedic surgical instruments customized to the particular patient based on the location at which the instrument is to be coupled to one or more bones of the patient, such as at the distal end of the patient's femur or proximal end of the patient's tibia. For example, in some embodiments, the customized patient-specific orthopedic surgical instruments may include one or more bone-contacting or facing surfaces having a negative contour that matches the contour of a portion of the relevant bone of the patient. As such, customized patient-specific orthopedic surgical instruments are configured to be coupled to the patient's bone in a unique location and position with respect to the patient's bony anatomy. That is, the negative contours of the bone-contacting surfaces are configured to receive a matching contour surface of the portion of the patient's b'one. As such, the orthopedic surgeon's guesswork and/or intra-operative decision-making with respect to the placement of the patient-specific orthopedic surgical instruments are reduced. For example, the orthopedic surgeon may not be required to locate landmarks of the patient's bone to facilitate the placement of the patient-specific orthopedic surgical instrument, which typically requires some amount of estimation on part of the surgeon. Rather, the orthopedic surgeon may simply couple the customized patient-specific orthopedic surgical instrument to the patient's bone in the unique, pre-planned location, as will be described in greater detail below.

The illustrative customized patient-specific orthopedic surgical system 10 includes a customized patient-specific orthopedic surgical instrument 12, a computer-controlled surgical milling machine 14 (hereinafter mill 14), and a computer 16 electrically coupled with the mill 14. As shown in FIGS. 1-7, the customized patient-specific orthopedic surgical instrument 12 is illustratively embodied as a customized patient-specific tibial surgical block 18 configured to be positioned in contact with the anterior side of the patient's tibia at the tibia's proximal end. In other embodiments, the customized patient-specific orthopedic surgical instrument 12 may be a femoral surgical block configured to be positioned in contact with anterior side of the patient's femur at the femur's distal end.

The customized patient-specific tibial surgical block 18 includes a customized patient-specific mounting block 20 (hereinafter mounting block 20) and a customized patient-specific guide block 22 (hereinafter guide block 22). As will be described in greater detail below, the guide block 22 is configured to be secured to the mounting block 20 to form the customized patient-specific tibial surgical block 18. The blocks 20, 22 may be formed from any suitable material such as, for example, a resilient plastic or metallic material. In one particular embodiment, the blocks 20, 22 may be formed from implant-grade metallic material such as titanium or cobalt chromium. In some embodiments, the blocks 20, 22 may be formed from the same material or different materials. For example, in one embodiment, the mounting block 20 may be formed from cobalt chromium while the guide block 22 may be formed from a resilient plastic. While the customized patient-specific tibial surgical block 18 has only the two pieces, it will be appreciated that in other embodiments the customized patient-specific tibial surgical block 18 may include additional pieces depending on the patient's specific bony anatomy.

The mounting block 20 includes a body 24 configured to contact a portion of the patient's tibia (or femur) during use. The body 24 includes a bone-contacting or bone-facing surface 26 and an outer surface 28 positioned opposite the bone-facing surface 26. A number of guide pin passageways or holes 30 are defined through the body 24 and extend from the outer surface 28 to the bone-facing surface 26. Each of the passageways 30 has an inner diameter sized to receive a respective guide pin to secure the mounting block 20 to the patient's tibia. In some embodiments, one or more of the passageways 30 may be oblique or otherwise angled with respect to the remaining passageways 30 to further secure the mounting block 20 to the patient's bone.

The bone-facing surface 26 of the body 24 includes a customized patient-specific negative contour 32 configured to receive the corresponding positive contour of the anterior side of the patient's tibia. It should be appreciated that in other embodiments the bone-facing surface 26 may include other customized patient-specific negative contours that are configured to receive other corresponding positive or negative contours of the patient's bone.

The body 24 of the mounting block 20 also includes a substantially flat upper surface 34 and a mounting bracket or locking structure 36 secured to the upper surface 34. The locking structure 36 is configured to separately mate with a corresponding locking structure 38 of the guide block 22 and another locking structure 40 of the mill 14. In that way, the guide block 22 or the mill 14 may be secured with the mounting block 20. As shown in FIG. 1, the locking structure 36 illustratively includes a pair of mounting pins 42 extending upwardly from the upper surface 34. Each of the pins 42 is embodied as an externally threaded rod sized to receive a corresponding internally threaded nut or locking member 44.

Figure 2:
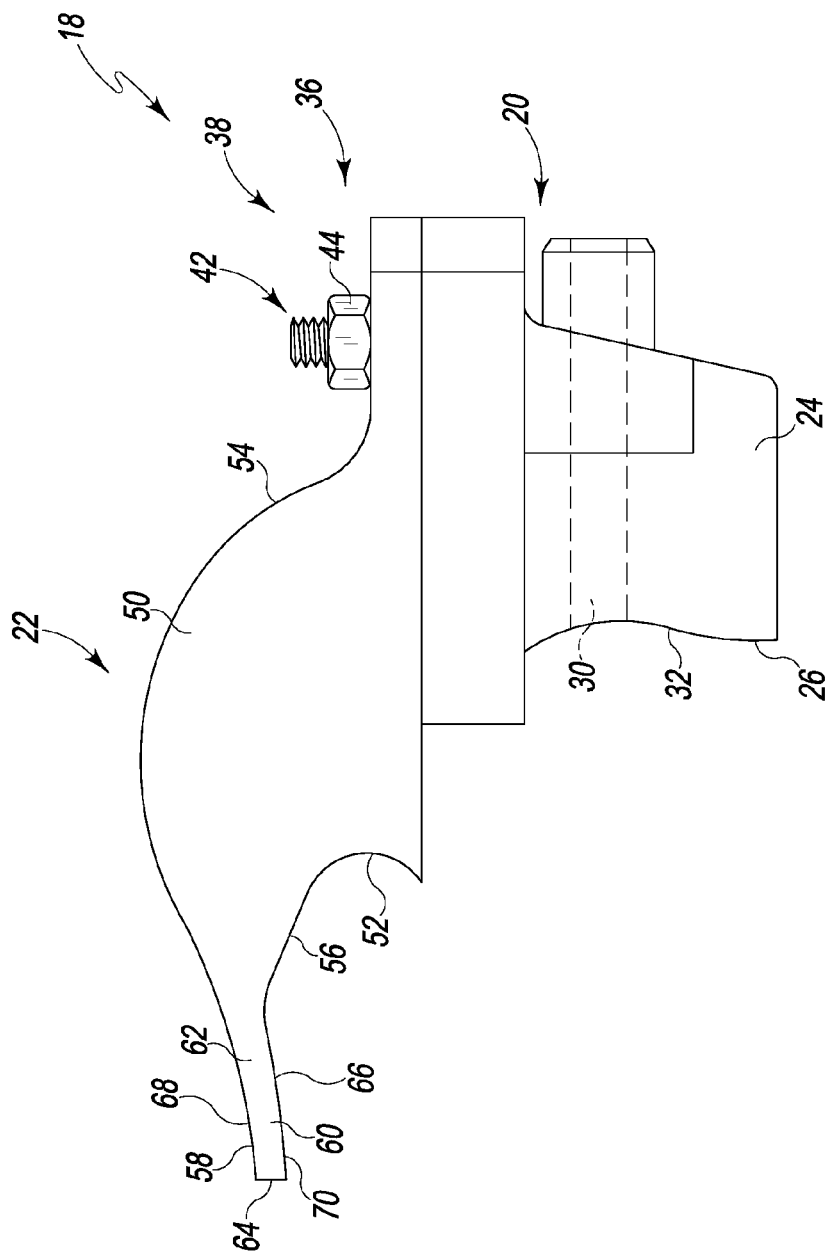
FIG. 2 is a side elevation view of the customized patient-specific surgical instrument of FIG. 1 assembled with the customized patient-specific mounting block secured to the customized patient-specific guide block.

The locking structures 38, 40 of the guide block 22 and the mill 14 are sized and configured to be separately mated with the locking structure 36. For example, the guide block 22 includes a pair of slots or passageways 46 extending therethrough, and each passageway 46 receives a corresponding mounting pin 42 of the mounting block 20. As shown in FIG. 2, the pins 42 extend through the passageways 46 when the guide block 22 is positioned in contact with the mounting block 20. The nuts 44 may be threaded onto the corresponding pins 42 to secure rigidly the guide block 22 to the mounting block 20. The mill 14 also includes a pair of passageways 48 extending therethrough, and each passageway 48 receives a corresponding mounting pin 42 of the mounting block 20 when the mill 14 is placed in contact with the mounting block 20. It will be appreciated that in other embodiments the locking structures 36, 38, 40 may be reversed such that the locking structure 36 of the mounting block 20 includes the pair of passageways and the locking structures 38, 40 include the mounting pins. Additionally, in other embodiments, the locking structures 36, 38, 40 may take the form of hooks, pins, latches, or other any other structure capable of being mated together to secure the mill 14 or the guide block 22 to the mounting block 20.

As shown in FIG. 1, the guide block 22 includes a body 50 configured to contact a portion of the patient's bone. The body 50 includes a bone-contacting or bone-facing surface 52 and an outer surface 54 positioned opposite the bone-facing surface 52. The bone-facing surface 52 includes a customized patient-specific negative contour 56 configured to receive the corresponding positive contour of the anterior side of the patient's tibia.

The guide block 22 also includes a pair of tabs 58 that extend away from the body 50. In FIG. 1, only one of the tabs 58 is shown because the tabs 58 have the same length. It will be appreciated that in other embodiments each tab 58 may have a different length. Each of the tabs 58 has an arm 60 extending from an anterior end 62 secured to the body 50 to a posterior end 64. The tabs 58 are tapered in the anterior-posterior direction such that the thickness of each tab 58 at the anterior end 62 is greater than the thickness at the posterior end 64. The tapering of each of the tabs 58 facilitates the insertion of the tabs 58 within the joint gap defined between the patient's femur and tibia. Each of the tabs 58 also includes a bone-contacting or bone-facing surface 66 and an outer surface 68 positioned opposite the bone-facing surface 66. The bone-facing surface 66 includes a negative contour 70 configured to receive a portion of the proximal end of the patient's tibia having a respective corresponding contour. It will be appreciated that in other embodiments the pair of tabs may be omitted depending on the bony anatomy of the patient and the type of surgical procedure.

The passageways 46 forming the locking structure 38 are defined in the body 50 of the guide block 22. Each passageway 46 extends from the outer surface 54 of the body 50 to a lower surface 72. When the guide block 22 is mated with the mounting block 20 as shown in FIG. 2, the lower surface 72 is placed in contact with the upper surface 34 of the mounting block 20. Additionally, each passageway 46 receives a corresponding mounting pin 42 of the mounting block 20.

When the customized patient-specific tibial surgical block 18 is assembled as shown in FIG. 2, each of its bone-facing surfaces 26, 52, 66 is configured to contact a different portion of the patient's tibia, thereby cooperating to place the surgical block 18 in a unique position and orientation. In some embodiments, the negative contours 32, 56, 70 of the bone-facing surfaces 26, 52, 66 of the surgical block 18 may be scaled or otherwise resized (e.g., enlarged) to compensate for the patient's cartilage or lack thereof.

Returning to FIG. 1, the mill 14 of the customized patient-specific orthopedic surgical system 10 includes a spindle 80 sized to receive a surgical tool 82. The surgical tool 82 may be a drill, an end mill cutter, or other cutting tool to be used to resect the patient's bone. As shown in FIG. 1, the mill 14 is embodied as a computer numerical controlled (or CNC) vertical mill that includes an electronically controlled drive system 84 configured to provide the spindle 80 with three degrees of freedom. In that way, the mill 14 may be used for 3-axis milling operations. In some embodiments, the mill 14 may be configured such that the spindle 80 has four or more degrees of freedom. In those embodiments, the mill 14 may be used for 4-axis or 5-axis milling operations. The mill 14 also includes a plurality of position sensors (not shown), each of which generates an electrical output signal indicative of the position of the spindle 80.

One example of a CNC vertical mill is the MDX-540 SRP® System, which is commercially available from Roland® Advanced Solutions Division of Roland DGA Corporation of Irvine, Calif. In the illustrative embodiment, the mill 14 is sized to the scale of the surgical operation. It should be appreciated that the mill 14 might include additional modifications depending on the nature of the surgical procedure. For example, the mill 14 may include actuators and motors to rotate the spindle relative to the horizontal or vertical axes. The mill 14 may also include a mechanical or electrical stop to prevent spindle overtravel.

As shown in FIG. 1, the mill 14 extends upwardly from a base 86. The base 86 includes a pair of flanges 88 having the pair of passageways 48 defined therein. As discussed above, the passageways 48 form the locking structure 40 in the illustrative embodiment. The passageways 48 extend from an upper surface 90 of the base 86 to a lower surface 92. When the mill 14 is mated with the mounting block 20, the lower surface 92 of the base 86 is placed in contact with the upper surface 34 of the mounting block 20 and each mounting pin 42 is received in a corresponding passageway 48.

The mill 14 is electronically coupled with the computer 16 via a communication link 94. The communication link 94 may be embodied as any type of communication link capable of facilitating communication between the computer 16 and the mill 14. For example, the communication link 94 may be embodied as any number of cables, wires, fiber optic cables, and/or the like.

As shown in FIG. 1, the computer 16 includes an input port 96 and a control panel 98. The input port 96 may be embodied as any type of input port configured to receive a portable media device (not shown) such as, for example, a compact disk, a digital video disk, a Universal Serial Bus (USB) device, or other portable media device. As such, the input port 96 may be embodied as any type of serial port, parallel port, flash drive port, or other data port capable of communicating with and storing data on the portable media device. The control panel 98 of the computer 16 has a number of controls (not shown), such as a keyboard, mouse, buttons, knobs, or other input devices used to control the operation of the mill 14. The control panel 98 also includes a display panel 102, such as, for example, a liquid crystal display (LCD) panel. In other embodiments, the control panel 98 may include only a touchscreen panel that is the sole control located on the control panel 98, thus permitting a user to control all user accessible operations of the mill 14 via the touchscreen panel.

The computer 16 also includes an electronic control unit or "electronic controller" 104 electronically coupled with the input port 96 and the control panel 98 via a number of communication links 106. Similar to the communication link 94, the communication links 106 may be embodied as any type of communication links capable of facilitating communication between the electronic controller 104, the input port 96, and control panel 98. For example, the communication links 106 may be embodied as any number of cables, wires, fiber optic cables, wireless signals, and/or the like.

The electronic controller 104 of the computer 16 is responsible for interpreting electrical signals sent by sensors associated with the mill 14 and for activating or energizing electronically controlled components associated with the mill 14. For example, the electronic controller 104 is configured to control the operation of the various components of the mill 14, including the drive system 84 and the spindle 80. The electronic controller 104 also monitors various signals from the control panel 98 and the position sensors. The electronic controller 104 also determines when various operations of the mill 14 should be performed. As will be described in more detail below with reference to FIG. 4, the electronic controller 104 is operable to control the components of the mill 14 such that the mill 14 performs the bone-cutting operation according to a predefined surgical plan.

To do so, the electronic controller 104 includes a number of electronic components commonly associated with electronic units utilized in the control of electromechanical systems. For example, the electronic controller 104 may include, amongst other components customarily included in such devices, a processor such as a microprocessor 108 and a memory device 110. The microprocessor 108 may be embodied as any type of processor including, for example, discrete processing circuitry (e.g., a collection of logic devices), general purpose integrated circuit(s), and/or application specific integrated circuit(s) (i.e., ASICs). The memory device 110 may be a programmable read-only memory device ("PROM") including erasable PROM's (EPROM's or EEPROM's). The memory device 110 is provided to store, amongst other things, instructions in the form of, for example, a software routine (or routines) which, when executed by the microprocessor 108, allows the electronic controller 104 to control operation of the mill 14.

The electronic controller 104 also includes an analog interface circuit 112. The analog interface circuit 112 converts the output signals from various sensors (e.g., the position sensors) into signals that are suitable for presentation to an input of the microprocessor 108. In particular, the analog interface circuit 112, by use of an analog-to-digital (A/D) converter (not shown) or the like, converts the analog signals generated by the sensors into digital signals for use by the microprocessor 108. It should be appreciated that the A/D converter may be embodied as a discrete device or number of devices, or may be integrated into the microprocessor 108. It should also be appreciated that if any one or more of the sensors associated with the mill 14 generate a digital output signal, the analog interface circuit 112 may be bypassed.

Similarly, the analog interface circuit 112 converts signals from the microprocessor 108 into output signals that are suitable for presentation to the electrically-controlled components associated with the mill 14 (e.g., the drive system 84). In particular, the analog interface circuit 112, by use of a digital-to-analog (D/A) converter (not shown) or the like, converts the digital signals generated by the microprocessor 108 into analog signals for use by the electronically controlled components associated with the mill 14. It should be appreciated that, similar to the A/D converter described above, the D/A converter may be embodied as a discrete device or number of devices, or may be integrated into the microprocessor 108. It should also be appreciated that if any one or more of the electronically controlled components associated with the mill 14 operate on a digital input signal, the analog interface circuit 112 may be bypassed.

Thus, the electronic controller 104 may control the operation of the mill 14 in accordance with the predefined surgical plan. In particular, the electronic controller 104 executes a routine including, amongst other things, a control scheme in which the electronic controller 104 monitors the outputs of the sensors associated with the mill 14 to control the inputs to the electronically controlled components associated therewith. To do so, the electronic controller 104 communicates with the sensors associated with the mill 14 to determine, amongst other things, the position of the spindle 80 relative to the patient's bone. The electronic controller 104 performs numerous calculations, either continuously or intermittently based on such data, including looking up values in preprogrammed tables, in order to execute algorithms to perform such functions as controlling the rotation speed of the spindle 80, controlling the movement of the spindle 80 relative to the patient's bone, and other functions.

Figure 3:
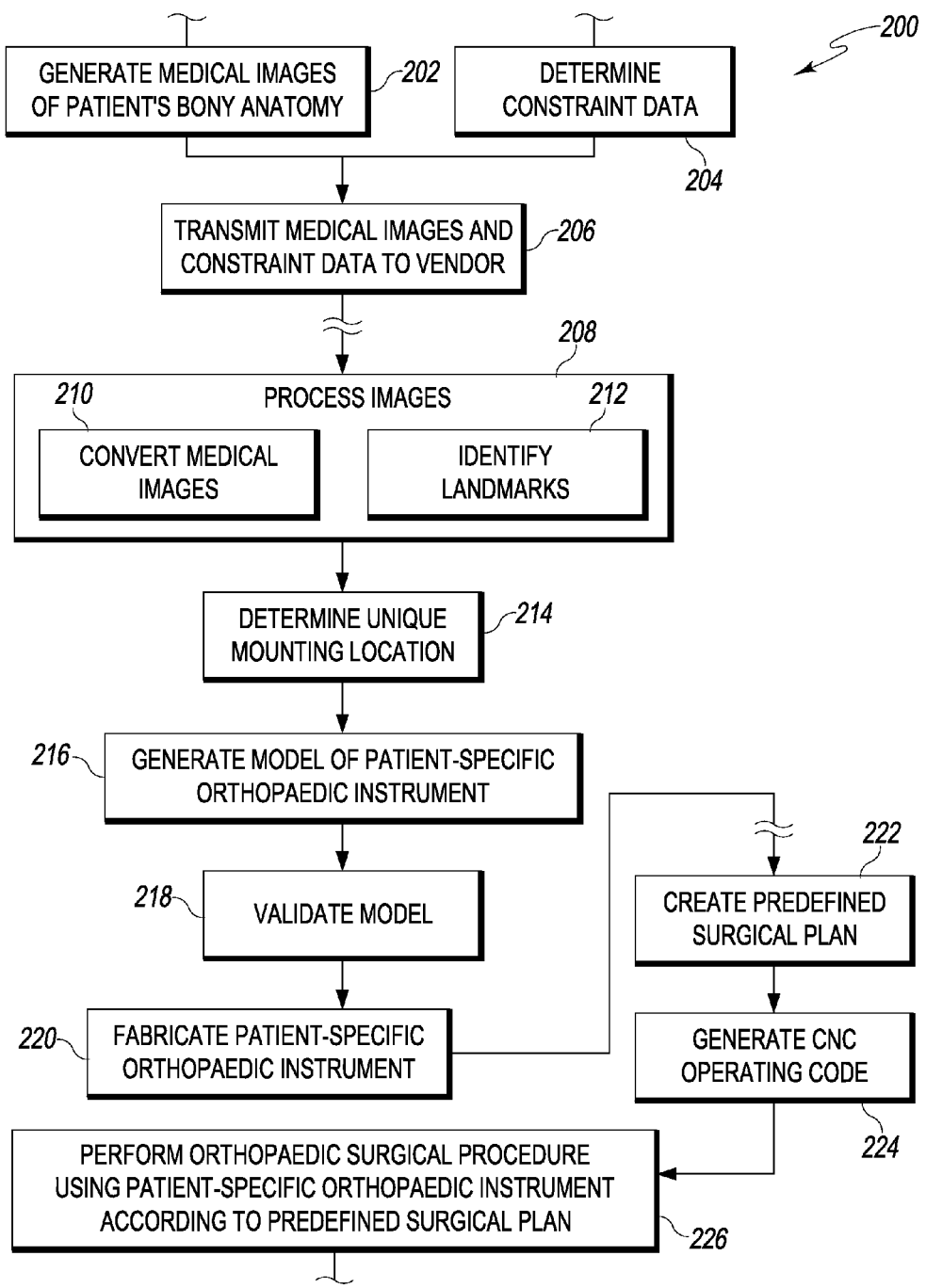
FIG. 3 is a simplified flow diagram of a method for designing and fabricating the customized patient-specific orthopedic surgical instrument of FIG. 1.

Referring now to FIG. 3, an algorithm 200 for fabricating the customized patient-specific tibial surgical block 18 and developing a predefined surgical plan is illustrated. The algorithm 200 includes steps 202 and 204, in which an orthopedic surgeon performs some of the pre-operative planning of the orthopedic surgical plan to be performed on a patient. The steps 202 and 204 may be performed in any order or contemporaneously with each other. In step 202, a number of medical images of the relevant bony anatomy or joint of the patient are generated. To do so, the orthopedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as any number of computed tomography (CT) images, magnetic resonance imaging (MRI) images, or other three-dimensional medical images. Additionally, or alternatively, as discussed in more detail below in regard to step 208, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's knee joint.

In step 204, the orthopedic surgeon may determine any additional pre-operative constraint data. The constraint data may be based on the orthopedic surgeon's preferences, preferences of the patient, anatomical aspects of the patient, guidelines established by the healthcare facility, or the like. For example, the constraint data may include the orthopedic surgeon's preference for a metal-on-metal interface, amount of inclination for implantation, the thickness of the bone to resect, size range of the orthopedic implant, and/or the like. In some embodiments, the orthopedic surgeon's preferences are saved as a surgeon's profile, which may be used as a default constraint values for further surgical plans.

In step 206, the medical images and the constraint data, if any, are transmitted or otherwise provided to an orthopedic surgical instrument vendor or manufacturer. The medical images and the constraint data may be transmitted to the vendor via electronic means such a network or the like. After the vendor has received the medical images and the constraint data, the vendor processes the images in step 208. The orthopedic surgical instrument vendor or manufacturer process the medical images to facilitate the determination of the bone cutting planes, implant sizing, and fabrication of the customized patient-specific tibial surgical block 18 as discussed in more detail below. For example, in step 210 the vendor may convert or otherwise generate three-dimensional images from the medical images. For example, in embodiments wherein the medical images are embodied as a number of two-dimensional images, the vendor may use a suitable computer algorithm to generate one or more three-dimensional images from the number of two-dimensional images. Additionally, in some embodiments, the medical images may be generated based on an established standard such as the Digital Imaging and Communications in Medicine (DICOM) standard. In such embodiments, an edge-detection, thresholding, watershed, or shape-matching algorithm may be used to convert or reconstruct images to a format acceptable in a computer aided design application or other image processing application. Further, in some embodiments, an algorithm may be used to account for tissue such as cartilage not discernable in the generated medical images. In such embodiments, any three-dimensional model of the patient-specific instrument (see, e.g., step 216 below) may be modified according to such algorithm to increase the fit and function of the instrument.

In step 212, the vendor may process the medical images, and/or the converted/reconstructed images from step 210, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In step 214, a unique mounting location for the customized patient-specific tibial surgical block 18 on the patient's bone is determined. As described in greater detail below, the predetermined, unique mounting location provides an accurate registration/reference point for the surgical tool 82 of the mill 14. The predetermined mounting location is determined based on, among other things, the type, size, and position of the orthopedic prosthesis to be used during the orthopedic surgical procedure, on the process images such as specific landmarks identified in the images, and on the constraint data supplied by the orthopedic surgeon in steps 204 and 206. The type and/or size of the orthopedic prosthesis may be determined based on the patient's anatomy and the constraint data. For example, the constraint data may dictate the type, make, model, size, or other characteristic of the orthopedic prosthesis. The selection of the orthopedic prosthesis may also be modified based on the medical images such that an orthopedic prosthesis that is usable with the bony anatomy of the patient and that matches the constraint data or preferences of the orthopedic surgeon is selected.

In addition to the type and size of the orthopedic prosthesis, the planned location and position of the orthopedic prosthesis relative to the patient's bony anatomy is determined. To do so, a digital template of the selected orthopedic prosthesis may be overlaid onto one or more of the processed medical images. The vendor may use any suitable algorithm to determine a recommended location and orientation of the orthopedic prosthesis (i.e., the digital template) with respect to the patient's bone based on the processed medical images (e.g., landmarks of the patient's bone defined in the images) and/or the constraint data. Additionally, any one or more other aspects of the patient's bony anatomy may be used to determine the proper positioning of the digital template.

In some embodiments, the digital template along with surgical alignment parameters may be presented to the orthopedic surgeon for approval. The approval document may include the implant's rotation with respect to bony landmarks such as the femoral epicondyle, posterior condyles, sulcus groove (Whiteside's line), and the mechanical axis as defined by the hip, knee, and/or ankle centers.

The planned mounting location for the customized patient-specific tibial surgical block 18 on the patient's bone(s) may then be determined based on the determined size, location, and orientation of the orthopedic prosthesis. In addition, other aspects of the patient's bony anatomy, as determined in step 212, may be used to determine or adjust the planned mounting location. For example, the determined mechanical axis, landmarks, and/or other determined aspects of the relevant bones of the patient may be used to determine the planned mounting location of the customized patient-specific tibial surgical block 18. Additionally, the travel of the spindle 80, the type of cutting tool 82, and the size of the mill 14 may also be used to determine the planned mounting location.

In step 216, a model of the customized patient-specific tibial surgical block 18 is generated. In some embodiments, the model is embodied as a three-dimensional rendering of the customized patient-specific tibial surgical block 18. In other embodiments, the model may be embodied as a mock-up or fast prototype of the customized patient-specific tibial surgical block 18. The particular shape or configuration of the customized patient-specific tibial surgical block 18 is determined based on the planned location of the surgical block 18 relative to the patient's bony anatomy. That is, the negative contours 32, 56, 70 of the bone-facing surfaces 26, 52, 66 match the contours of a portion of the bony anatomy of the patient such that the customized patient-specific tibial surgical block 18 may be coupled to the bony anatomy of the patient in the unique mounting location determined in step 214. In some embodiments, the negative contours 32, 56, 70 of the bone-facing surfaces 26, 52, 66 of the surgical block 18 may be scaled or otherwise resized (e.g., enlarged) based on the images generated in step 202 to compensate for the patient's cartilage or lack thereof.

After the model of the customized patient-specific tibial surgical block 18 has been generated in step 216, the model is validated in step 218. The model may be validated by, for example, analyzing the rendered model while coupled to the three-dimensional model of the patient's anatomy to verify the mounting location and the position of the mill 14 relative to the patient's tibia when the mill 14 is attached to the mounting block 20. Additionally, the model may be validated by transmitting or otherwise providing the model generated in step 216 to the orthopedic surgeon for review. For example, in embodiments wherein the model is a three-dimensional rendered model, the model along with the three-dimensional images of the patient's relevant bone(s) may be transmitted to the surgeon for review. In embodiments wherein the model is a physical prototype, the model may be shipped to the orthopedic surgeon for validation.

After the model has been validated in step 218, customized patient-specific tibial surgical block 18 is fabricated in step 220. The customized patient-specific tibial surgical block 18 may be fabricated using any suitable fabrication device and method. Additionally, the customized patient-specific orthopedic instrument may be formed from any suitable material such as a metallic material, a plastic material, or combination thereof depending on, for example, the intended use of the instrument. The fabricated customized patient-specific tibial surgical block 18 is subsequently shipped or otherwise provided to the orthopedic surgeon.

In step 222, the orthopedic surgeon may use the model generated in step 216 and three-dimensional images of the patent's bony anatomy from step 202 to complete pre-operative planning and develop a predefined surgical plan. The term "predefined surgical plan" as used herein refers to the preplanned sequence of steps to be performed as part of the orthopedic surgical procedure. The preplanned sequence may include, among many others things, the process of locating the customized patient-specific tibial surgical block 18 on the patient's bone in the unique mounting location, the series of cuts and resections to be made to the bone by the surgeon or the mill 14, and the procedure for implanting the orthopedic prosthesis.

In step 224, the computer code for operating the mill 14 is generated. To do so, the model generated in step 216, three-dimensional images of the patent's bony anatomy from step 202, and the predefined surgical plan developed in step 222 are entered into computer-aided manufacturing (CAM) software and converted into instructions written in the specific programming language of the mill 14. The CAM software may be located in the computer 16 such that the computer operating code can be generated locally. Alternatively, the software may be located on a remote machine and the computer operating code may be later transferred to the computer 16.

Once the computer operating code is generated, the orthopedic surgeon can validate the code by running simulations to verify that the mill 14 will operate according to the predefined surgical plan. For example, the surgeon may verify that the mill 14 performs all of the cuts required in the preplanned order. Additionally, the surgeon may verify that the predetermined mounting location of the customized patient-specific surgical block 18 provides an accurate reference point for the surgical tool 82 of the mill 14. The validated computer operating code may then be loaded onto the computer 16 to control the operation of the mill 14.

Figure 4:
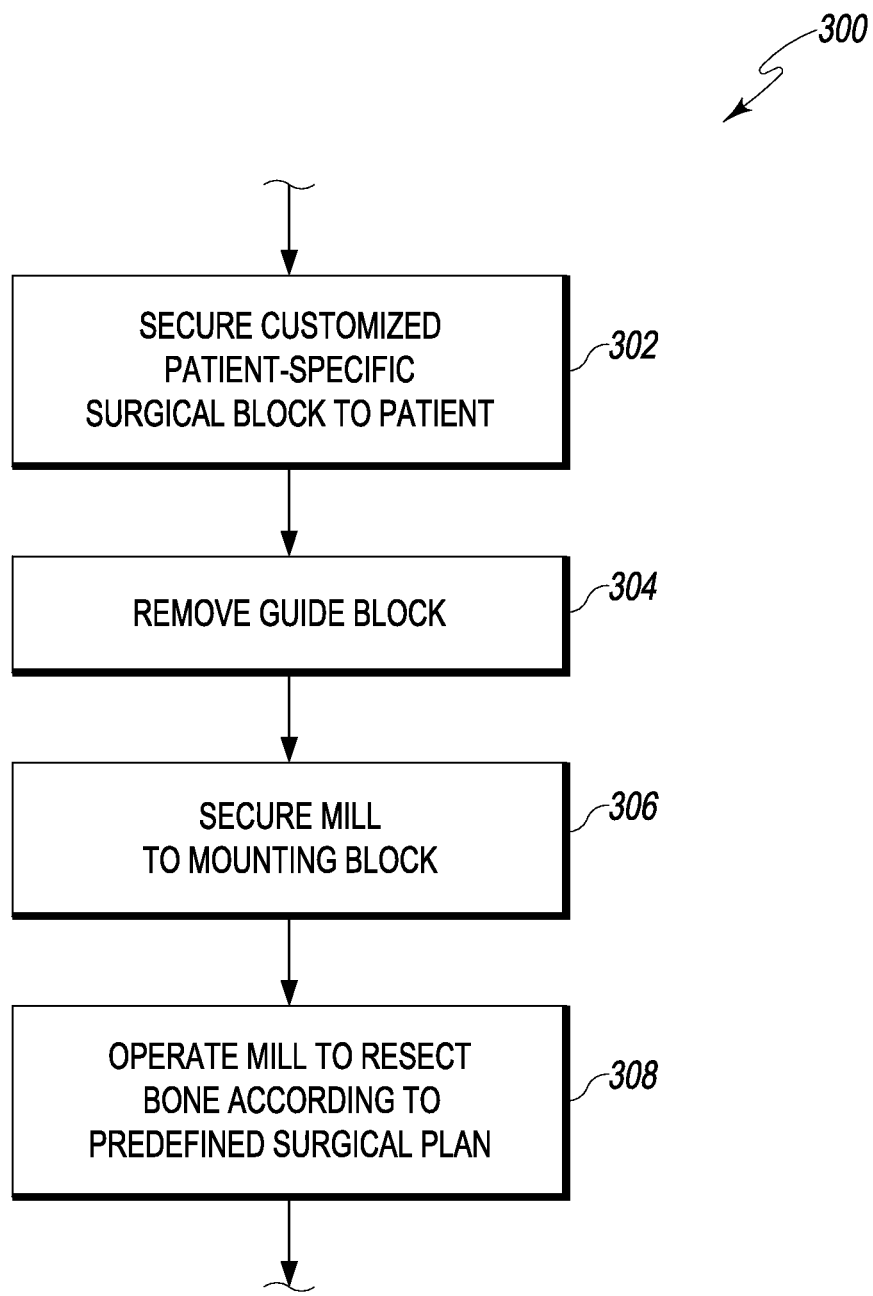
FIG. 4 is a simplified flow diagram of a method of performing a bone resecting procedure using the customized patient-specific orthopedic surgical system of FIG. 1.

In step 226, the surgeon performs the predefined orthopedic surgical procedure using the customized patient-specific orthopedic surgical system 10. An illustrative orthopedic surgical procedure 300 using the customized patient-specific orthopedic surgical system 10 is shown in FIG. 4. As discussed above, because the orthopedic surgeon does not need to determine the proper location of the orthopedic surgical instrument intra-operatively, which typically requires some amount of estimation on part of the surgeon, the guesswork and/or intra-operative decision-making on part of the orthopedic surgeon is reduced.

Figure 5:
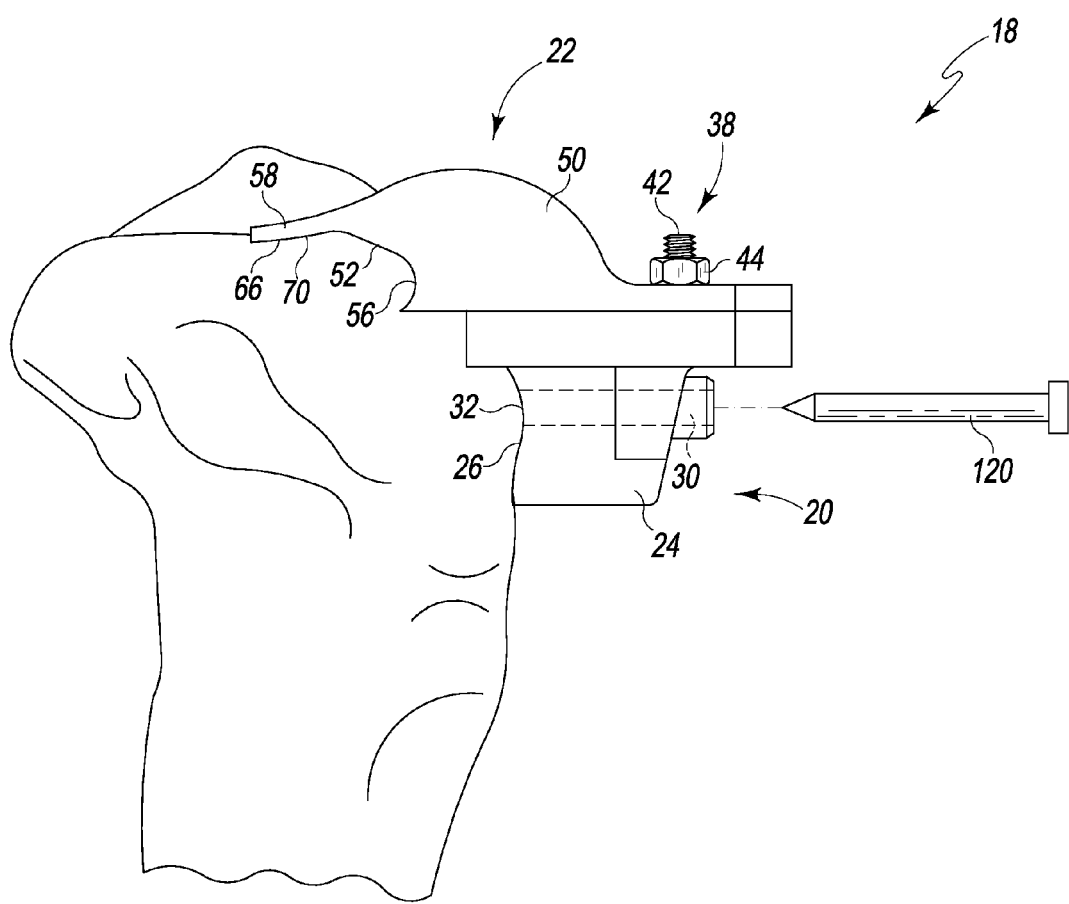
FIG. 5 is a side elevation view of the customized patient-specific surgical instrument of FIG. 1 positioned on a bone of a patient and assembled with the customized patient-specific mounting block secured to the customized patient-specific guide block.

Referring now to FIG. 4, in step 302, the surgeon positions the assembled customized patient-specific tibial surgical block 18 on the patient's tibia. The assembled surgical block 18 is positioned on the patient's tibia in the unique, predetermined mounting location because the blocks 20, 22 are customized to match the bone of the particular patient, as shown in FIG. 5. Because the bone-facing surfaces 26, 52, 66 of the blocks 20, 22 include customized patient-specific negative contours 32, 56, 70, the assembled surgical block 18 is positioned on the patient's tibia such that the corresponding contours of the surface of the patient's tibia are received in the negative contours 32, 56, 70. For example, when the surgical block 18 is properly positioned, the contour 32 of the mounting block 20 receives the corresponding positive contour of the anterior side of the patient's tibia. The customized patient-specific negative contours 56, 70 of the guide block 22 also receive the corresponding positive contour of the proximal end of the patient's tibia when the assembled surgical block 18 is properly positioned at the predetermined mounting location.

After the assembled surgical block 18 is properly positioned, the surgeon secures the assembled surgical block 18 to the patient's tibia (or femur) using a plurality of bone pins 120. To do so, the surgeon drills a pilot hole in the patient's tibia near its proximal end using each of the passageways 30 as drilling guides. As shown in FIG. 5, the surgeon may then insert a bone pin 120 through each of the passageways 30 and into the corresponding pilot hole defined in the patient's tibia.

Figure 6:
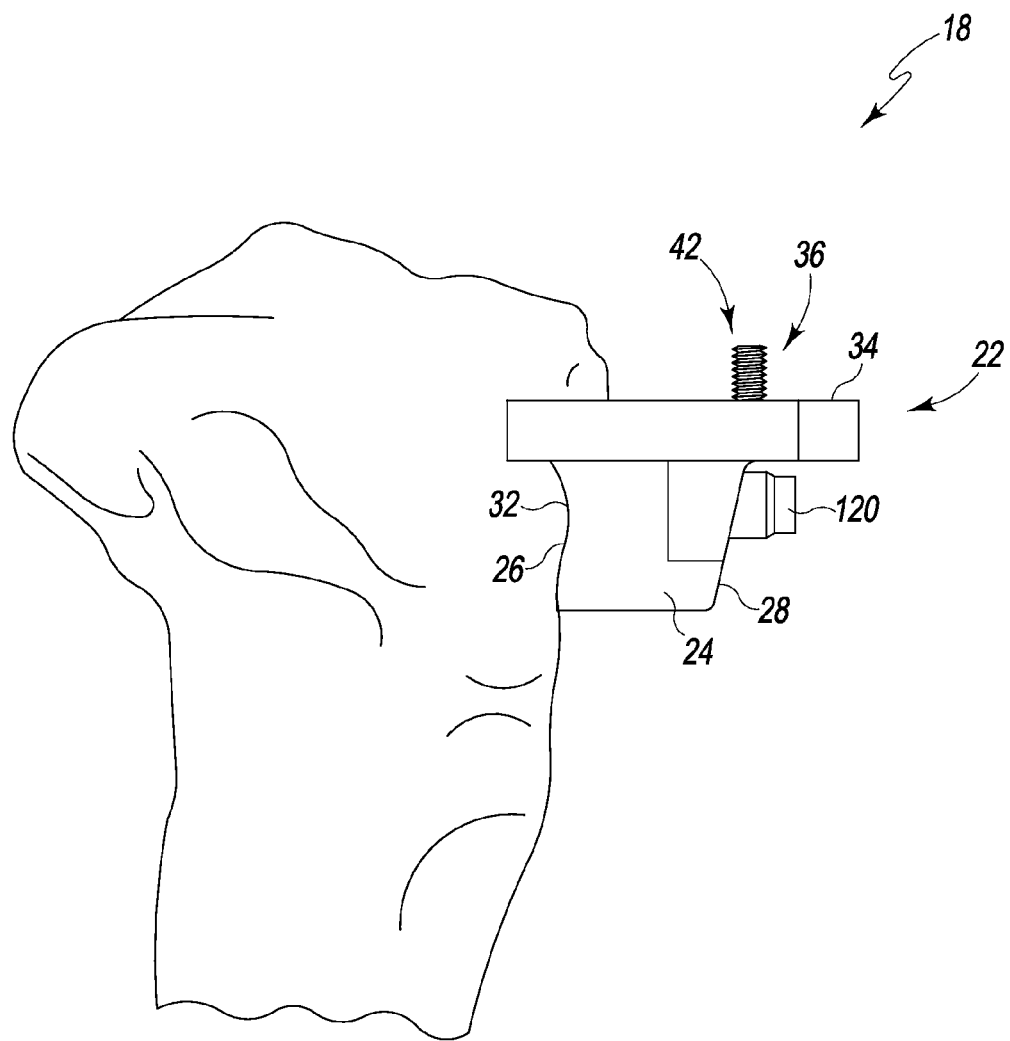
FIG. 6 is a side elevation view of the customized patient-specific mounting block of FIG. 1 positioned on a bone of a patient with the customized patient-specific guide block removed.

In step 304, the surgeon removes the guide block 22 from the mounting block 20. To do so, the surgeon decouples the locking structure 38 of the guide block 22 from the locking structure 36 of the mounting block 20. In the illustrative embodiment, the surgeon unthreads each of the nuts 44 from the threaded pins 42. Once the nuts 44 are removed, the surgeon may then remove the guide block 22 from the mounting block 20. As shown in FIG. 6, the bone pins 120 ensure that the mounting block 20 remains secured to the patient's tibia at the predetermined mounting location after the guide block 22 is removed.

Figure 7:
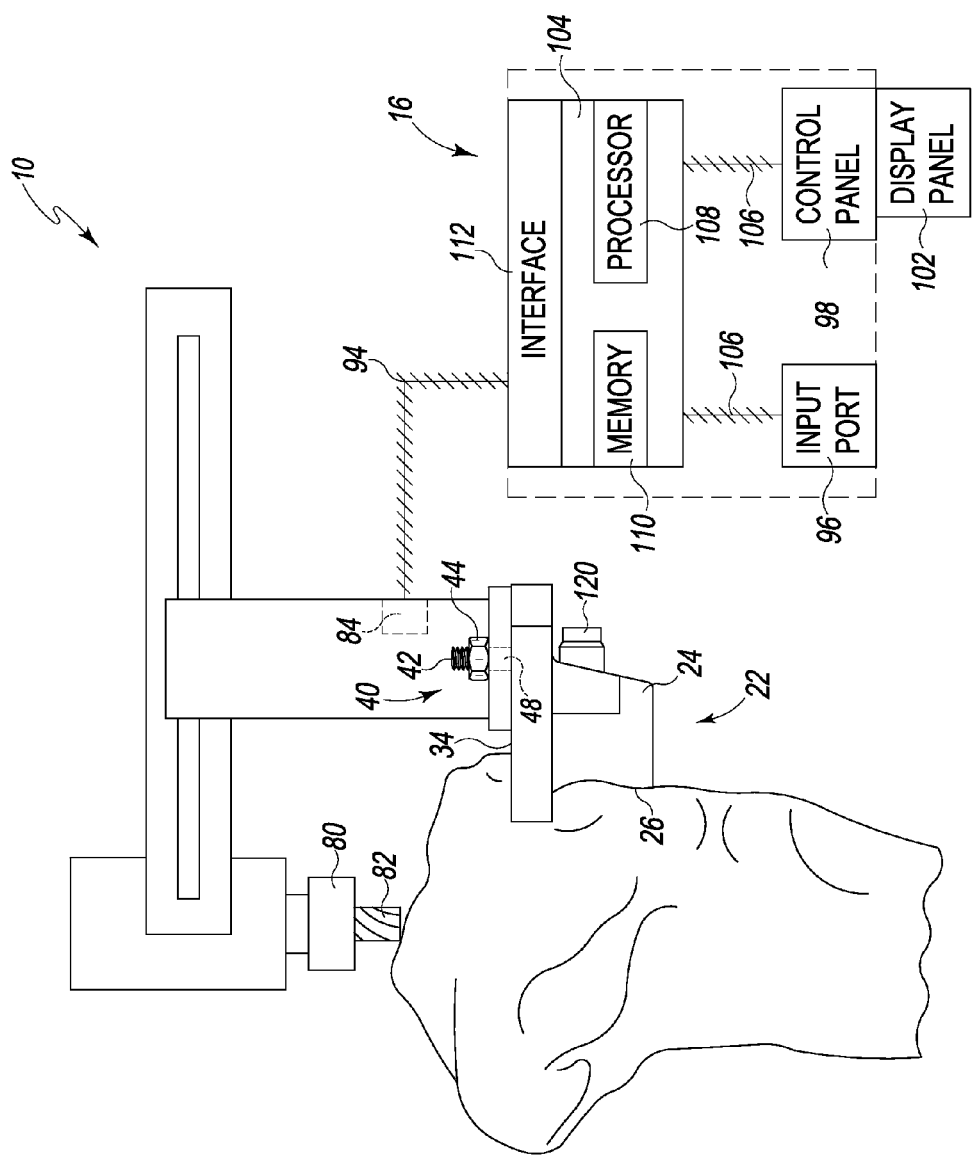
FIG. 7 is a side elevation view of the computer-controlled milling machine secured to the customized patient-specific mounting block of FIG. 1.

The surgeon may then attach the mill 14 to the mounting block 20 in step 306. To do so, the surgeon couples the locking structure 40 of the mill 14 to the locking structure 36 of the mounting block 20. As shown in FIG. 7, the passageways 48 formed in the base 86 of the mill 14 receive the threaded pins 42 extending upwardly from the body 24 of the mounting block 20 when the mill 14 is properly positioned. The surgeon then threads nuts 44 onto the corresponding pins 42 to rigidly secure the mill 14 to the mounting block 20.

In step 308, the surgeon operates the mill 14 to resect the patient's bone. Because the mounting block 20 is located at a unique, preplanned position on the patient's tibia, the mounting block 20 provides an accurate reference point for the start or "home" position of cutting tool 82 of the mill 14 relative to the patient's tibia. Using the control panel 98, the surgeon may activate the mill 14 and command the microprocessor 108 to execute the computer operating code such that the mill 14 resects the patient's bone according to the predefined orthopedic surgical procedure. In the illustrative embodiment, the mill 14 resects the proximal end of the tibia to prepare the bone for a tibial orthopedic prosthesis. It will be appreciated that in other embodiments the mill 14 may resect other portions of a patient's bone such as, for example, the distal end of a femur.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. For example, although specific data rate values and ranges and specific frequency values and ranges have been disclosed in various embodiments, it should be appreciated that data rates and/or frequencies near such values may be in used in other embodiments.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A customized patient-specific orthopaedic surgical system comprising:
   a first surgical block comprising (i) a first bone-facing surface having a first customized patient-specific negative contour to receive a first corresponding contour of an anterior side of a bone of a patient, and (ii) a first mounting surface having a first locking structure,
   a second surgical block configured to be coupled to the first surgical block, comprising (i) a second bone-facing surface having a second customized patient-specific negative contour to receive a second corresponding contour of a first end of the bone of the patient, and (ii) a second mounting surface having a second locking structure configured to couple with the first locking structure to secure the first surgical block to the second surgical block, and
   a computer-controlled milling machine configured to be coupled to the first surgical block, comprising a milling head and a base, the base having a third mounting surface having a third locking structure configured to couple with the first locking structure to secure the milling machine to the first surgical block in place of the second surgical block.

2. The orthopaedic surgical system of claim 1, wherein the first surgical block further comprises a pair of mounting pin holes defined therein that extend from the first bone-facing surface to an outer surface of the first surgical block, the outer surface being positioned opposite the first bone-facing surface.

3. The orthopaedic surgical system of claim 1, further comprising:
   an electronic controller electrically coupled to the computer-controlled milling machine,
   wherein the electronic controller comprises (i) a processor, and (ii) a memory device electrically coupled to the processor, the memory device having stored therein a plurality of instructions that, when executed by the processor, cause the processor to operate the computer-controlled milling machine to resect the bone of the patient in accordance with a predefined surgical plan.

4. The orthopaedic surgical system of claim 1, wherein:
   the first locking structure includes a pair of mounting pins extending upwardly from the first mounting surface, and
   the second locking structure includes a pair of passageways defined in the second mounting surface that are sized and positioned to receive the pair of mounting pins.

5. The orthopaedic surgical system of claim 4, wherein the third mounting surface includes a second pair of passageways defined therein sized and positioned to receive the pair of mounting pins.

6. The orthopaedic surgical system of claim 5, wherein each mounting pin is an externally threaded rod sized to receive a corresponding internally threaded nut.

7. A customized patient-specific orthopaedic surgical system comprising:
   a customized patient-specific surgical block comprising:
   a first piece including (i) a first bone-facing surface having a first customized patient-specific negative contour to receive a first corresponding contour of a bone of a patient, and (ii) a first locking structure, and
   a second piece including (i) a second bone-facing surface having a second customized patient-specific negative contour configured to receive a second corresponding contour of the bone of the patient, and (ii) a second locking structure configured to be separately mated and couple with the first locking structure to secure the first piece to the second piece; and a computer-controlled milling machine including a milling head and a base, wherein the base has a third locking structure configured to be separately mated with the first locking structure in place of the second piece.

8. The orthopaedic surgical system of claim 7, wherein the customized patient-specific surgical block is a customized patient-specific femoral surgical block.

9. The orthopaedic surgical system of claim 7, wherein the customized patient-specific surgical block is a customized patient-specific tibial surgical block.

10. The orthopaedic surgical system of claim 7, wherein the first piece further comprises a pair of mounting pin holes defined therein, and the pair of mounting pin holes extend from the first bone-facing surface to an outer surface positioned opposite the first bone-facing surface.

11. The orthopaedic surgical system of claim 7, further comprising:

an electronic controller electrically coupled to the computer-controlled milling machine, wherein the electronic controller comprises (i) a processor, and (ii) a memory device electrically coupled to the processor, the memory device having stored therein a plurality of instructions that, when executed by the processor, cause the processor to operate the computer-controlled milling machine in accordance with a predefined surgical plan.

\* \* \* \* \*